(12) United States Patent
Kennedy

(10) Patent No.: US 10,201,162 B2
(45) Date of Patent: *Feb. 12, 2019

(54) PSEUDOMONAS SPECIES HAVING WEED SUPPRESSIVE ACTIVITY AND BENIGN SOIL SURVIVAL TRAITS FOR ANNUAL GRASS WEED MANAGEMENT

(71) Applicant: The United States of America, as represented by the Secretary of Agriculture, Washington, DC (US)

(72) Inventor: Ann C. Kennedy, Pullman, WA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/404,965

(22) Filed: Jan. 12, 2017

(65) Prior Publication Data
US 2017/0118993 A1 May 4, 2017

Related U.S. Application Data

(63) Continuation of application No. 14/270,006, filed on May 5, 2014, now Pat. No. 9,578,884.

(51) Int. Cl.
*A01N 63/00* (2006.01)
*C12R 1/39* (2006.01)
*C12N 1/00* (2006.01)

(52) U.S. Cl.
CPC .............. *A01N 63/00* (2013.01); *C12R 1/39* (2013.01); *C12N 1/00* (2013.01)

(58) Field of Classification Search
CPC ........ A01N 63/00; A01N 63/02; A01N 63/04; A01N 51/00; C12R 1/38; C12R 1/39
See application file for complete search history.

(56) References Cited

U.S. PATENT DOCUMENTS 9,578,884 B2 * 2/2017 Kennedy ............... A01N 63/00
2006/0093536 A1 5/2006 Selby
(Continued)

FOREIGN PATENT DOCUMENTS

EP 0348120 A2 12/1989
EP 1023832 A1 8/2000

OTHER PUBLICATIONS

Boxall, Bettina, "Scientists may have a new weapon in cheatgrass war", LA Times, Apr. 1, 2013, 1 page.
(Continued)

*Primary Examiner* — Aaron J Kosar
(74) *Attorney, Agent, or Firm* — David L. Marks; John D. Fado; Gail E. Poulos

(57) ABSTRACT

In exemplary embodiments, the disclosure provides weed-suppressive *Pseudomonas fluorescens* strains effective for controlling one or more invasive grass weeds that are members selected from the group consisting of downy brome (cheatgrass, *Bromus tectorum* L.), medusahead (*Taeniatherum caput medusae* (L.) Nevski) and jointed goatgrass (*Aegilops cylindrica* L.). In exemplary embodiments, the weed-suppressive *Pseudomonas fluorescens* bacterial strain is a member selected from the group consisting of: *Pseudomonas fluorescens* strain ACK55, *Pseudomonas fluorescens* strain NKK78 and *Pseudomonas fluorescens* strain SMK69. In still other exemplary embodiments the disclosure provides methods for selecting weed-suppressive *Pseudomonas fluorescens* strains.

3 Claims, 1 Drawing Sheet
(1 of 1 Drawing Sheet(s) Filed in Color)

Specification includes a Sequence Listing.

(56) References Cited

U.S. PATENT DOCUMENTS

2006/0147438 A1     7/2006   Azevedo et al.
2010/0093536 A1     4/2010   Armstrong et al.

OTHER PUBLICATIONS

Ibekwe, A. Mark, Ann C. Kennedy and Tami L. Stubbs, "An assessment of environmental conditions for control of downy brome by Pseudomonas fluorescens D7", (2010) Int. J. Environmental Technology and Management 12(1):27-46.

Nudel et al., "A New Biological Management Option against Cheatgrass Raises Hope of Western Land Managers", Fish and Wildlfe Services PAcific Region News Release, Published Apr. 1, 2013, <url:www.fws.gov/pacific/news.cfm?id=2144375216>, 3 pages.

Banowetz, Gary M. et al., "Germation-Arrest Factor (GAF): Biological properties of a novel, naturally-occurring herbicide produced by selected isolates of rhizosphere bacteria", (2008) Biological Control 46:380-390.

Dooley, Sandra R. et al., "Characterizing the interaction between a fungal seed pathogen and a deleterious-rhizobacterium for biological control of cheatgrass", (2010) Biological Control 53:197-203.

\* cited by examiner

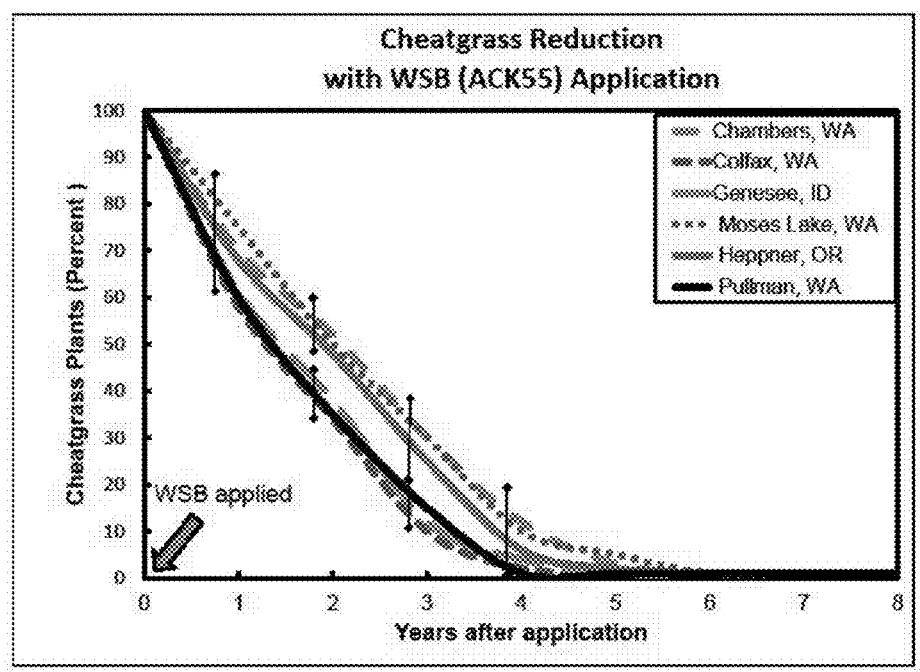

PSEUDOMONAS SPECIES HAVING WEED SUPPRESSIVE ACTIVITY AND BENIGN SOIL SURVIVAL TRAITS FOR ANNUAL GRASS WEED MANAGEMENT

CROSS-REFERENCE OF THE APPLICATION

This patent application is a continuation application of and claims priority to U.S. patent application Ser. No. 14/270,006 filed on May 5, 2014, now U.S. Pat. No. 9,578,884 issued on Feb. 28, 2017.

FIELD OF THE INVENTION

The disclosure relates to the biocontrol of grass weeds.

BACKGROUND OF THE INVENTION

Historically, nearly 220 million acres of sagebrush steppe existed in North America, making it one of the most widespread habitats in the continent. Sagebrush ecosystems are found throughout western North America providing diverse habitats for a variety of flora and fauna. Numerous species of the sagebrush steppe are sagebrush obligates and thus, are dependent on the sagebrush biome for their survival. Exemplary sagebrush dependent species include Sage Grouse (*Centrocercus urophasianus*), Brewer's Sparrow (*Spizella breweri*), Sage Thrasher (*Oreoscopies montanus*), Sage Sparrow (*Amphispiza belli*), Pygmy Rabbit (*Brachylagus idahoensis*), Sagebrush Lizard (*Sceloporis graciosus*), Sagebrush Vole (*Lemmiscus curtatus*), Pronghorn Antelope (*Antilocapra americana*) to name a few.

Unfortunately, human activity and invasion by non-native plant species has resulted in the loss of over half of the sagebrush ecosystem. The threats to the ecosystem continue to this day. Indeed, of the remaining 100 million acres of sagebrush steppe habitat in the Intermountain West, over half are infested by invasive grasses such as e.g., downy brome (*Bromus tectorum* L., aka cheatgrass). Invasive grass weeds are adapted to a wide range of annual precipitation, soil conditions and disturbance thus, there is little in the natural ecosystem to contain their spread.

Invasive grass weeds also exert negative impacts on croplands and agriculture. At least 15 million acres of cropland in the west are infested with some level of downy brome. The mat-like rooting system of downy brome and its ability to grow further into the winter season than wheat, allows downy brome to easily outcompete wheat. Indeed, downy brome is very competitive with winter wheat for soil water and nutrients. Fifty downy brome plants $ft^{-2}$ can remove available soil water to a depth of about two feet. Thus, a moderate infestation of two to 10 plants $ft^{-2}$ reduces wheat yields 30-50%. A heavy infestation can reduce yields by 80%. Although herbicides are available, most are expensive, vary in effectiveness, and do not reduce the seed bank. Seed bank longevity is typically underestimated and some downy brome seeds can remain in the soil for years.

In addition to competing for water resources, downy brome produces significant amounts of dead, above-ground biomass that accelerates wildfire in both rangeland and in cropland. The dead, above-ground biomass comprises a fine, dense mat of highly flammable fuel susceptible to ignition, which accelerates fire cycles. Accordingly, fire size, intensity, and frequency have increased dramatically with the expansion of annual grass weed infestations. In addition to disrupting the ecology and ecosystem, fire can be devastating to rangeland and standing crops, and leaves the soil more vulnerable to erosion and runoff.

Unfortunately, while many approaches have been taken to control invasive grass weeds, so far, none have had widespread success.

Thus, what is needed in the art are compositions and methods that permit control of invasive grass weeds without negatively affecting native plants or crops, and not changing the soil ecosystem, thereby allowing for preservation and restoration of sagebrush-steppe habitats and increased agricultural productivity. Fortunately, as will be clear from the following disclosure, the present invention provides for these and other needs.

SUMMARY OF THE INVENTION

In one aspect, the present disclosure provides a weed-suppressive *Pseudomonas fluorescens* strain effective for controlling one or more invasive grass weeds that are members selected from the group consisting of downy brome (cheatgrass, *Bromus tectorum* L.), medusahead (*Taeniatherum caput-medusae* (L.) Nevski) and jointed goatgrass (*Aegilops cylindrica* L.). In an exemplary embodiment, the weed-suppressive *Pseudomonas fluorescens* strain controls the invasive grass weed downy brome (cheatgrass, *Bromus tectorum* L.). In another exemplary embodiment, the weed-suppressive *Pseudomonas fluorescens* strain is a member selected from the group consisting of: *Pseudomonas fluorescens* strain ACK55, *Pseudomonas fluorescens* strain NKK78 and *Pseudomonas fluorescens* strain SMK69. In another exemplary embodiment, the weed-suppressive *Pseudomonas fluorescens* strain is *Pseudomonas fluorescens* strain ACK55.

In another aspect, the disclosure provides a weed-suppressive *Pseudomonas fluorescens* strain known as *P.f.* ACK55 deposited under the Budapest Treaty with the Agricultural Research Service Culture Collection (NRRL), National Center for Agricultural Utilization Research, Agricultural Research Service, U.S. Department of Agriculture, 1815 North University Street, Peoria Ill. 61604, U.S.A. on Aug. 15, 2013, having NRRL accession number NRRL B-50848.

In another aspect, the disclosure provides a weed-suppressive *Pseudomonas fluorescens* strain known as *P.f.* NKK78 deposited under the Budapest Treaty with the Agricultural Research Service Culture Collection (NRRL), National Center for Agricultural Utilization Research, Agricultural Research Service, U.S. Department of Agriculture, 1815 North University Street, Peoria, Ill. 61604, U.S.A. on Aug. 15, 2013, having NRRL accession number NRRL B-50849.

In another aspect, the disclosure provides a weed-suppressive *Pseudomonas fluorescens* strain known as *P.f.* SMK69, deposited under the Budapest Treaty with the Agricultural Research Service Culture Collection (NRRL), National Center for Agricultural Utilization Research, Agricultural Research Service, U.S. Department of Agriculture, 1815 North University Street, Peoria Ill. 61604, U.S.A. on Aug. 15, 2013, having NRRL accession number NRRL B-50850.

In another aspect, the disclosure provides a method for controlling invasive grass weeds in an area of land, the method comprising: (i) applying a weed-suppressive *Pseudomonas fluorescens* strain to the land. In an exemplary embodiment, the applying is accomplished by mixing the weed-suppressive *Pseudomonas fluorescens* strain into the land. In another exemplary embodiment, the applying is accomplished by spraying the weed-suppressive suppressive *Pseudomonas fluorescens* strain onto the land. In another exemplary embodiment, the weed-suppressive *Pseudomonas fluorescens* strain is a member selected from the group consisting of *Pseudomonas fluorescens* strain ACK55, *Pseudomonas fluorescens* strain NKK78, and *Pseudomonas fluorescens* strain SMK69.

In another aspect, the disclosure provides a method for isolating weed-suppressive *Pseudomonas fluorescens* strains effective for controlling one or more invasive grass weeds that are members selected from the group consisting of downy brome (cheatgrass, *Bromus tectorum* L.), medusahead (*Taeniatherum caput-medusae* (L.) Nevski) and jointed goatgrass (*Aegilops cylindrica* L.) the method for isolating weed-suppressive bacteria comprising: (i) freeze-thaw sampling soil to obtain *Pseudomonas fluorescens* strains; (ii) assaying the *Pseudomonas fluorescens* obtained in step (i) for their ability to inhibit grass weed growth; (iii) selecting *Pseudomonas fluorescens* that inhibit grass-weed growth; (iv) testing the *Pseudomonas fluorescens* selected in step (iii) against desirable plant species to identify *Pseudomonas fluorescens* that do not inhibit growth of the desirable plant species; (v) selecting *Pseudomonas fluorescens* that do not inhibit growth of desirable plant species; (vi) testing the *Pseudomonas fluorescens* selected in step (v) for antimicrobial activity; (vii) selecting *Pseudomonas fluorescens* that do not exhibit antimicrobial activity; (viii) testing the *Pseudomonas fluorescens* selected in step (vii) for the absence of enzyme activity; (ix) selecting *Pseudomonas fluorescens* that do not exhibit enzyme activity; (x) testing the *Pseudomonas fluorescens* selected in step (ix) for protein secretion; (xi) selecting *Pseudomonas fluorescens* that do not exhibit protein secretion; (xii) testing the *Pseudomonas fluorescens* selected in step (xi) for their effect on macrofauna; (xiii) selecting *Pseudomonas fluorescens* that do not effect macrofauna; (xiv) testing the *Pseudomonas fluorescens* selected in step (xiii) for the ability to withstand freeze drying; (xv) selecting *Pseudomonas fluorescens* that withstand freeze drying; (xvi) testing the *Pseudomonas fluorescens* selected in step (xv) in soil for their ability to inhibit grass weeds without deleteriously affecting desirable plant species; and (xvii) selecting *Pseudomonas fluorescens* that inhibit grass weeds without deleteriously affecting desirable plant species in soil; thereby isolating weed-suppressive *Pseudomonas fluorescens* strains effective for controlling one or more invasive grass weeds that are members selected from the group consisting of downy brome (cheatgrass, *Bromus tectorum* L.), medusahead (*Taeniatherum caput-medusae* (L.) Nevski) and jointed goatgrass (*Aegilops cylindrica* L.).

Other features, objects and advantages of the invention will be apparent from the detailed description that follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 The effect of weed-suppressive bacteria (*P.f.* ACK55) on downy brome populations with time. Bacteria were applied once as a spray to sites across the Pacific Northwest at $10^8$ log cells $m^{-2}$ in the fall of the first year.

DETAILED DESCRIPTION OF THE INVENTION

Definitions

The term "grass weed", "grass-weed" or "invasive grass weed" as used herein, refers to non-native (exotic) invasive grasses that grow profusely and damage or have the potential to damage native ecosystems and compete with crop species. Typically, non-native invasive grass weeds are introduced as a direct or indirect result of human activity. Having been moved by humans to a region in which they did not evolve, invasive grass weeds typically are able to flourish, crowding out native vegetation and the wildlife that feeds on it. In general, invasive grass weeds have a competitive advantage because they are no longer controlled by their natural predators, and thus, can quickly spread out of control. In some exemplary embodiments, invasive grass weeds change ecosystem processes such as hydrology, fire regimes, and soil chemistry. Exemplary invasive grass weeds include, but are not limited to downy brome/cheatgrass (*Bromus tectorum* L.), medusahead (*Taeniatherum caput-medusae* (L.) Nevski), and jointed goatgrass (*Aegilops cylindrica* L.).

As used herein, the term "control", "controls", or "controlling" as in e.g., the phrase: "controls invasive grass weeds", "controlling" invasive grass weeds, as used herein, refers to preventing spread or invasion, reducing the severity of already infested/invaded areas or suppression or eradication of the invasive grass weeds e.g. cheatgrass, medusahead, Ventenata or other invasive weed grasses whose "control" is desired. Indeed, "controlling" as used herein refers to any indication of success in prevention, elimination, reduction or amelioration of an invasive grass weed population or an invasive grass weed problem. In exemplary embodiments, "control" of invasive grass weeds as disclosed herein, is brought about by inhibiting growth of the invasive grass weed(s). In other exemplary embodiments, "control" of invasive grass weeds as disclosed herein, is brought about by reducing the effects of invasive grass weed(s). In still other exemplary embodiments, "control" of invasive grass weeds as disclosed herein, is brought about by preventing further invasions of invasive grass weed(s).

The expression "inhibit the growth of an annual grass weed", "inhibit the growth of grass weeds", "inhibiting the growth of invasive grass weeds", "inhibition of grass weed" or any equivalent grammatical expression as used herein, refers to inhibition or suppression of grass weed growth. In an exemplary embodiment, inhibition of annual grass weed provides at least a 50% reduction in root growth (length) of a grass weed treated with weed-suppressive bacteria as compared to a control grass weed that is untreated with weed-suppressive bacteria. In other exemplary embodiments, inhibition of annual grass weed provides at least a 60% reduction, at least a 70% reduction or more in root growth (length) of a grass weed treated with weed-suppressive bacteria as compared to a control grass weed that is untreated with weed-suppressive bacteria. In another exemplary embodiment, inhibition of an annual grass weed provides at least a 20% reduction or more in germination of a grass weed treated with weed-suppressive bacteria as compared to a control grass weed that is not treated with weed-suppressive bacteria. In another exemplary embodiment, inhibition of an annual grass weed provides at least a 30% reduction, at least a 40% reduction at least a 50% reduction, a 60% reduction or more in germination of a grass weed treated with weed-suppressive bacteria as compared to a control grass weed that is untreated with weed-suppressive bacteria. Thus, in exemplary embodiments, "inhibition of grass weeds" provides for "control" of grass weeds.

The expression "inhibitory amount" as used herein refers to the amount or titer of weed-suppressive bacteria that, when mixed with a corresponding quantity of soil, seed or substrate is effective for inhibiting the growth of grass weeds and thereby providing for control of invasive grass weeds.

The term "weed-suppressive soil bacteria" as used herein, refers to bacteria, particularly *Pseudomonas* spp. that, when applied in an inhibitory amount, to soil, seed or plants is effective for controlling invasive grass weeds.

The terms "isolated" or "purified," as used herein, refer to material that is substantially or essentially free from components that normally accompany it as found in its native state. In an exemplary embodiment, purity and homogeneity are determined by measuring bacterial titers using methods known in the art. A bacterium that is the predominant species present in a preparation is substantially purified or substantially isolated. Typically, the term "purified" means that the bacterium is typically about 100% pure.

The expression "without negatively affecting the desired plant species" as used herein, refers to a bacterial strain that when applied to desirable plant seedlings as disclosed herein see e.g. *Agar bioassay for weed suppression* hereinbelow, reduces root growth of the treated desirable plant seedlings less than 25% by comparison to control desirable plant seedlings that are not treated with bacteria.

The expression "desired plant species" as used herein, refers to plants that humans wish/desire/prefer to cultivate or establish. Cultivated plants include, but are not limited to crop plants. Thus, in some exemplary embodiments, a "desired plant species" is an economically important crop species e.g., wheat. Humans may also wish to reestablish or protect native habitats and the flora and fauna comprising the habitat. Thus, in other exemplary embodiments a "desired plant species" is a native plant species e.g. sagebrush, or near-native plant species that comprise a particular habitat e.g., sagebrush steppe habitat.

The term "crops" or "crop plants" as used herein refers to a volunteered or cultivated plant wherein the plant or part thereof is harvested by a human at some point of its growth stage. In exemplary embodiments, crop species are harvested for use as food, clothing, livestock feed, medicine, biofuel, etc. "Crops" are typically regarded as "desired plant species". Exemplary "crops" include, but are not limited to wheat, corn, barley, etc.

The expression "native plant species" as used herein refers to plants that are endemic (indigenous) or naturalized to a given area/habitat. In an exemplary embodiment, sagebrush is a native species endemic to the sagebrush steppe habitat. Typically, native plant species grow naturally in a particular region without direct or indirect human actions.

The term "near-native plant species" as used herein, refers to plants that are naturalized to a given area. "Near-native plant species" have typically been naturalized for a long period of time such that they are so well established as to be almost considered as "native plant species". Typically, "near-native plant species" act similarly to native plants, but may not be found growing naturally in a particular region or area, and may have had direct or indirect human intervention.

The expression "no protein secretions" as used herein, refers to no protein secretions as described herein below in Section II. C. (2) step 6.

I. Introduction

Weed-suppressive bacterial strains disclosed herein inter alia inhibit the growth of invasive annual grass weeds in cropland, rangeland, road sides, right-of-ways, turf, sod, etc., without negatively affecting desired plant species e.g., perennial bunchgrass, sagebrush, wheat, etc. In exemplary embodiments weed-suppressive bacteria are applied by spraying a field or other area to be treated with an inhibitory amount of the weed-suppressive bacteria. In other exemplary embodiments, weed-suppressive bacteria are applied in an inhibitory amount to the subsurface of the soil, e.g., below the surface of the soil. In still other exemplary embodiments, weed-suppressive bacteria are applied to the seeds of desirable plant species in an amount sufficient to inhibit the weed when planted in the field.

Exemplary grass weeds e.g., cheatgrass, medusahead and jointed goatgrass are annual grass weeds that are invading the lands of the western United States. These exotic, invasive grass species negatively affect shrub-steppe habitats and croplands of the western United States by e.g., increasing wildfire frequencies thereby removing long-lived perennial species, thus facilitating further invasion by invasive grass weeds and/or by out-competing agricultural crops for water resources.

Unfortunately, attempts to remove invasive grass weeds and restore invaded areas have, until now, found few practical solutions. Indeed, even herbicides, which have been the best solution so far, do not reduce the weed seed bank. As is well known in the art, the weed seed bank is a critical factor permitting invasive grass weeds to propagate year after year.

Fortunately, disclosed in detail hereinbelow are weed-suppressive bacteria that control invasive grass weeds by inter alia reducing growth and/or preventing establishment and/or by reducing the weed seed bank.

II. Weed-suppressive bacteria

A. General

Disclosed herein are native soil bacteria that suppress grass weeds e.g., downy brome, medusahead and jointed goatgrass, while not injuring desired plant species such as e.g., crops and native or near-native plant species. The disclosed weed-suppressive bacteria are *Pseudomonas fluorescens* strains isolated from soil. Exemplary weed-suppressive bacteria include, but are not limited to, *Pseudomonas fluorescens* isolates disclosed herein as *P.f.* ACK55, *P.f.* NKK78 and/or *P.f.* SMK69.

The disclosed weed-suppressive soil bacteria, once applied to a soil, establish in the soil and suppress invasive grass weeds by e.g., reducing the seed bank, seedling root growth and seed production over several years. In an exemplary embodiment, one application of weed-suppressive bacteria reduces downy brome populations to near zero after five years (see e.g., FIG. 1).

Typically, weed-suppressive soil bacteria applied to field soil exist in high numbers in the winter and early spring when annual invasive grass weeds are just starting to grow. Without being bound by theory it is believed that the weed-suppressive bacteria disclosed herein control invasive grass weeds by way of secretion of a large molecular weight compound that inhibits lipopolysaccharide production and cell elongation in the roots of growing grass weeds. In addition, if the bacteria are present when the root starts emerging from the seed, which is the time of tiller initiation, the bacteria also reduce tiller formation. The suppressive compound is highly labile and can only be partially purified. The compound contains chromopeptides, other peptides, and fatty acid esters in a lipopolysaccharide matrix. Separation of any of the components from the complex resulted in nearly complete loss of activity against downy brome, jointed goatgrass and medusahead. In addition to inhibiting root-cell elongation and tiller initiation, this compound reduces the vigor of grass weed seedlings and overwintering, lowers seed production and reduces viability of the grass weed seed bank.

The compound secreted by the weed-suppressive bacteria is made up of multiple parts and it breaks down very readily. All the parts are needed for activity. The genes responsible for the inhibitory compound made by the weed-suppressive bacteria disclosed herein are found in many locations on the chromosome. Without being bound by theory, it is believed that the fact that the genes needed to produce the suppressive compound are at several different places on the chromosome reduces the chance that the full complement of genes could be transferred to another bacterium. In addition, if a mutation could occur in one of the multiple locations, the weed-suppressive compound would not be produced. The multiple locations reduce the risk of mutations occurring that change the structure of the compound and ensure that it is highly unlikely that a mutation would alter the genes such that the suppressive compounds would change to attack another plant species. Thus, weed-suppressive bacteria disclosed herein are species specific, inhibiting only a few specific species of grasses while not affecting the growth of almost all other grasses nor broadleaf plants.

The grass weed-suppression is due to the production of a compound that specifically targets invasive grass weeds and these bacteria are selected because they have little antimicrobial activity toward fungi and other bacteria. Thus, they do not cause major change to the soil microbial community. However, for the same reason, survival of the weed-suppressive bacteria is critical to success of weed-suppressive bacteria as a biocontrol agent. Indeed, weed suppression does not occur if the bacteria die before they can establish on roots and residue in the soil.

Once applied to the soil surface or provided as a seed coating, weed-suppressive bacteria are carried into the soil by water e.g., by rain, irrigation, etc. The bacteria grow on residue, seeds or roots, then move to the roots of the target grass weeds, grass weed seeds or young grass weed seedlings and inhibit annual grass weed root-cell elongation. The weed-suppressive bacteria colonize the outside of the roots only. They do not enter the cells as they do not have the enzymes to break down the cell wall or membrane and they have minimal protein secretions. Thus, weed-suppressive bacteria do not harm the majority of plants.

As noted above, the suppressive compound secreted by the weed-suppressive bacteria inhibits lipopolysaccharide production in the cell wall and/or cell membrane of colonized weed roots thereby reducing root-cell wall elongation. The weed-suppressive bacteria colonize the roots of any plant species, but the suppressive compound only inhibits the growth of the three weed species. Thus, if inhibition of cell elongation occurs early in the seedling life, e.g., because weed-suppressive bacteria are established in the soils at the time the seedling is germinating, tiller initiation is reduced. Visual effects are any one or more of a red color of the plant leaves due to stress and anthocyanin production, stunted plants with few tillers and few seeds produced. Typically, the soil seed bank is also reduced.

Weed-suppressive bacteria are active in the soil below the soil surface only during cool temperatures in late winter to early spring. These bacteria inhibit cell elongation of the grass weed root and reduce root growth, which reduces the grass weed competitiveness. By reducing the competitive ability of the annual grass weeds in the early spring or late fall, the other plant species are able to establish and grow and then the bacteria and the beneficial plant work to reduce the weed further.

Typically, effective control of invasive grass weeds e.g., downy brome (cheatgrass, *Bromus tectorum* L.), medusahead (*Taeniatherum caput medusae* (L.) Nevski), and jointed goatgrass (*Aegilops cylindrica* L.) improves as the bacteria become established in the soil. Thus, maximum control/suppression of invasive grass weeds by weed-suppressive bacteria may take as long as 2 to 5 years though results may also be seen at earlier times post application. In general, application of the bacterium into hot, dry soil dramatically reduces the survival of the bacterium and does not result in control or suppression of invasive grass weeds. However, application of the bacterium under cool, wet conditions allows the bacterium to grow and establish in the soil. If dry conditions occur after the bacteria can establish in the soil, weeds are stressed by both bacteria and drought and often weed growth is reduced further than either stress alone.

B. Exemplary *Pseudomonas fluorescens* having Weed-Suppressive Activity

1. *P.f.* ACK55

*Pseudomonas fluorescens* strain ACK55 is a naturally occurring rod-shaped bacterium that produces a labile compound that inhibits downy brome, medusahead and jointed goatgrass root cell elongation. This compound selectively inhibits the root cell elongation and tiller initiation of these seeds. Because of its selectivity, this bacterium is useful for management of invasive grass weeds such as e.g., downy brome, medusahead and jointed goatgrass in rangeland, cropland, pasture, turf, sod production, golf courses, road sides and road cuts, construction sites, and right-of-ways (road, rail, pipeline, electrical), etc. A detailed description of the characteristics is provided immediately hereinbelow.

*Pseudomonas fluorescens* strain ACK55 (Pf. ACK55) is a motile, Gram-negative rod. It has two polar flagella and a thick exopolysaccharide coating. Taxonomically, it is identified as *Pseudomonas fluorescens* biovar II or 'B' group with some similarity to biovar I or 'A' group from MIDI analysis and it grows within pH ranges from 3.8 to 8.5. *P.f.* ACK55 is an aerobe, but can function as a facultative anaerobe with nitrate as the substrate. *P.f.* ACK55 produces a large molecular weight compound with tertiary structure that inhibits lipopolysaccharide production and cell elongation in the roots of accessions of downy brome (cheatgrass, *Bromus tectorum* L.), medusahead (*Taeniatherum caput medusae* (L.) Nevski), and jointed goatgrass (*Aegilops cylindrica* L.). The active fraction complex is highly labile and can only be partially purified. The compound, however, contains chromopeptides, other peptides, and fatty acid esters in a lipopolysaccharide matrix. Separation of any of the components from the complex resulted in nearly complete loss of activity against downy brome, medusahead, and jointed goatgrass. The genes responsible for the weed-suppressive compound are found on the chromosome at multiple positions, all of which are needed for activity. *P.f.* ACK55 produces a limited amount of pyoverdin, arginine dihydrolase, lecithinase, thioquinolobactin, and protcatechuate decarboxylase. *P.f.* ACK55 is resistant to penicillin and novobicin. *P.f.* ACK55 gives a positive result to the oxidase and catalase tests. *P.f.* ACK55 has no anti-fungal activity, and no anti-bacterial activity. *P.f.* ACK55 does not produce 2,4-diacetylphloroglucinol; pyrrolnitrin; pyoluteorin; or hydrogen cyanide. *P.f.* ACK55 does not produce pyocyanins, chlororaphin, phenazine, phenoxazone, amino phenol, lipase, or xanthomonadins. *P.f.* ACK55 is indole negative; methyl-red negative; does not denitrify; does not accumulate nor hydrolyze poly-B-hyroxybutyrate; does not hydrolyze starch; nor does it grow on $H_2$. *P.f.* ACK55 does not secrete Type 1, 2 or 3 secretions, produces no enzymes that degrade plant cell membranes.

A host-range study investigating more than two hundred select plant species showed that only downy brome, medusahead, and jointed goatgrass were significantly inhibited by the bacterium. *P.f.* ACK55 grows well under cooler conditions of the fall coinciding with the early root growth of the fall annual weeds. P.f. ACK55 declines with summer temperatures, and by doing so it does not overrun the native soil bacteria. P.f. ACK55 is not a competitive bacterium, although it can survive at low number over a few years. P.f. ACK55 moves in soil by traveling on the growing root or with water. P.f. ACK55 growing on the root delivers the inhibitory compound. As the root grows, P.f. ACK55 is carried along and they grow down the root.

2. P.f. NKK78

Pseudomonas fluorescens strain NKK78 (P.f. NKK78) is a naturally occurring rod-shaped bacterium that produces a labile compound that inhibits downy brome, medusahead and jointed goatgrass root cell elongation. This compound selectively inhibits the root cell elongation and tiller initiation of these seeds. Because of its selectivity, this bacterium is useful for management of invasive grass weeds such as downy brome, medusahead and jointed goatgrass in rangeland, cropland, pasture, turf, sod production, golf courses, road sides and road cuts, construction sites, and right-of-ways (road, rail, pipeline, electrical), etc. A detailed description of the bacterial characteristics is provided immediately below.

Pseudomonas fluorescens strain NKK78 is a motile, Gram-negative rod. It has two polar flagella and a thick polysaccharide coating. Taxonomically, it is identified as Pseudomonas fluorescens biovar I or 'A' group from MIDI analysis and it grows within pH ranges from 3.8 to 8.5. P.f. NKK78 is an aerobe, but can function as a facultative anaerobe with nitrate as the substrate. P.f. NKK78 produces a large molecular weight compound with tertiary structure that inhibits lipopolysaccharide production and cell elongation in the roots of accessions of downy brome (cheatgrass, Bromus tectorum L.), medusahead (Taeniatherum caput medusae (L.) Nevski), and jointed goatgrass (Aegilops cylindrica L.). The active fraction complex is highly labile and can only be partially purified. The compound however contains chromopeptides, other peptides, and fatty acid esters in a lipopolysaccharide matrix. Separation of any of the components from the complex resulted in nearly complete loss of activity against downy brome, medusahead, and jointed goatgrass. The genes responsible for the weed-suppressive compound are found on the chromosome at multiple positions, all of which are needed for activity. P.f. NKK78 produces a limited amount of pyoverdin, arginine dihydrolase, lecithinase, thioquinolobactin, and protcatechuate decarboxylase. P.f. ACK55 is resistant to penicillin and novobicin. P.f. NKK78 gives a positive result to the oxidase and catalase tests. P.f. NKK78 has no anti-fungal activity, and no anti-bacterial activity. P.f. NKK78 does not produce 2,4-diacetylphloroglucinol; pyrrolnitrin; pyoluteorin; or hydrogen cyanide. P.f. NKK78 does not produce pyocyanins, chlororaphin, phenazine, phenoxazone, amino phenol, lipase, or xanthomonadins. P.f. NKK78 is indole negative; methyl-red negative; does not denitrify; does not accumulate nor hydrolyze poly-B-hyroxybutyrate; does not hydrolyze starch; nor does it grow on $H_2$. P.f. NKK78 does not secrete Type 1, 2 or 3 secretions, and it produces no enzymes that degrade plant cell membranes.

A host-range study investigating more than two hundred select plant species showed that only downy brome, medusahead, and jointed goatgrass were significantly inhibited by the bacteria. P.f. NKK78 grows well under cooler conditions of the fall coinciding with the early root growth of the fall annual weeds. P.f. NKK78 declines with summer temperatures, and by doing so, it does not overrun the native soil bacteria. P.f. NKK78 is not a competitive bacterium, though it can survive at low number over a few years. P.f. NKK78 moves in soil by traveling on the growing root or with water. P.f. NKK78 growing on the root delivers the inhibitory compound. As the root grows, P.f. NKK78 is carried along and they grow down the root.

3. P.f. SMK69

Pseudomonas fluorescens strain SMK69 (P.f. SMK69) is a naturally occurring rod-shaped bacterium that produces a labile compound that inhibits downy brome, medusahead and jointed goatgrass root cell elongation. This compound selectively inhibits the root cell elongation and tiller initiation of these seeds. Because of its selectivity, this bacterium is useful for management of invasive grass weeds such as downy brome, medusahead and jointed goatgrass in rangeland, cropland, pasture, turf, sod production, golf courses, road sides and road cuts, construction sites, and right-of-ways (road, rail, pipeline, electrical), etc. A detailed description of the bacterial characteristics is provided immediately below.

Pseudomonas fluorescens strain SMK69 is a motile, Gram-negative rod. It has two polar flagella and a thick polysaccharide coating. Taxonomically, it is identified as Pseudomonas fluorescens biovar I or 'A' group with some similarity to biovar II or 'B' group from MIDI analysis and it grows within pH ranges from 3.8 to 8.5. P.f. SMK69 is an aerobe, but can function as a facultative anaerobe with nitrate as the substrate. P.f. SMK69 produces a large molecular weight compound with tertiary structure that inhibits lipopolysaccharide production and cell elongation in the roots of accessions of downy brome (cheatgrass, Bromus tectorum L.), medusahead (Taeniatherum caput medusae (L.) Nevski), and jointed goatgrass (Aegilops cylindrica L.). The active fraction complex is highly labile and can only be partially purified. The compound however contains chromopeptides, other peptides, and fatty acid esters in a lipopolysaccharide matrix. Separation of any of the components from the complex resulted in nearly complete loss of activity against downy brome, medusahead, and jointed goatgrass. The genes responsible for the weed-suppressive compound are found on the chromosome at multiple positions, all of which are needed for activity. P.f. SMK69 produces a limited amount of pyoverdin, arginine dihydrolase, lecithinase, thioquinolobactin, and protcatechuate decarboxylase. P.f. SMK69 is resistant to penicillin and novobicin. P.f. SMK69 gives a positive result to the oxidase and catalase tests. P.f. SMK69 has no anti-fungal activity, and no anti-bacterial activity. P.f. SMK69 does not produce 2,4-diacetylphloroglucinol; pyrrolnitrin; pyoluteorin; or hydrogen cyanide. P.f. SMK69 does not produce pyocyanins, chlororaphin, phenazine, phenoxazone, amino phenol, lipase, or xanthomonadins. P.f. SMK69 is indole negative; methyl-red negative; does not denitrify; does not accumulate nor hydrolyze poly-B-hyroxybutyrate; does not hydrolyze starch; nor does it grow on $H_2$. P.f. SMK69 does not secrete Type 1, 2 or 3 secretions, and it produces no enzymes that degrade plant cell membranes.

A host-range study investigating more than two hundred select plant species showed that only downy brome, medusahead, and jointed goatgrass were significantly inhibited by the bacteria. P.f. SMK69 grows well under cooler conditions of the fall coinciding with the early root growth of the fall annual weeds. P.f. SMK69 declines with summer temperatures, and by doing so, it does not overrun the native soil bacteria. P.f. SMK69 is not a competitive bacterium, although it can survive at low number over a few years. P.f. SMK69 moves in soil by traveling on the growing root or with water. P.f. SMK69 growing on the root delivers the inhibitory compound. As the root grows, *P.f.* SMK69 is carried along and they grow down the root.

C. Identifying *Pseudomonas fluorescens* Having Weed-Suppressive Activity

1. General Methods

This disclosure utilizes routine techniques in the field of microbiology and microbial genetics. Basic texts disclosing the general methods of use in this disclosure include e.g., *Methods for General and Molecular Microbiology*, 3rd ed., C. A. Reddy, et al., eds. ASM Press (2007); and *Encyclopedia of Microbiology*, 2nd ed., Joshua Lederburg, ed., Academic Press (2000).

Unless otherwise noted, technical terms are used according to conventional usage. Definitions of common terms in microbiology maybe found in e.g., *Microbiology* By Cliffs Notes, I. Edward Alcamo, Wiley (1996); *Encyclopedia of Microbiology*, (2000) supra; *Dictionary of Microbiology and Molecular Biology* 3rd ed., Paul Singleton and Diana Sainsbury, Wiley (2007).

This disclosure also utilizes routine techniques in the field of microbial genetics. Basic texts disclosing the general methods and concepts used herein include e.g., *Pseudomonas: Volume 6: Molecular Microbiology*, by Juan L. Ramos, Alain Filloux, Springer (2010); *Modern Microbial Genetics*, $2^{nd}$ ed., Uldis N. Streips, Ronald E. Yasbin, eds., Wiley-Liss (2002); *Pseudomonas: Genomics and Molecular Biology* Pierre Cornelis, ed., Caister Academic Press (2008).

2. Selecting *Pseudomonas fluorescens* having weed-suppressive activity

The screening method comprises:

Step 1. Freeze- Thaw soil sampling.

Weed-suppressive bacteria increase in cell numbers in the soil only in the late fall, winter and early spring (<10° C.; <50° F.) especially directly after a hard freeze followed by a daytime thaw. Thus, in an exemplary embodiment, bacteria are isolated from soils that have experienced at least 3 days of a hard freeze (<–1.1° C.; <30° F.) and are presently experiencing a thaw (>4.4° C.; >40° F.). Bacteria are isolated by sampling soil or plant roots from the thawed area; placing the soil or roots in sterile dilution blanks containing sterile water; and shaking the mixture vigorously to remove organisms clinging to the root or soil surface. Then serial dilutions are prepared and spread plated on to a selective medium such as King's Medium B supplemented with novobiocin, penicillin, and cycloheximide (KMB NPC) using methods known in the art (see e.g., Sands and Rovira, Applied Microbiology 20:513-514 (1970)), and incubated at 15° C. (59° F.).

Step 2. Agar Bioassay for Weed Suppression

The bacteria are assayed for their ability to suppress root growth of the annual grass weeds and many accessions of each weed. Bacterial strains isolated in step 1 are screened to select those strains that inhibit annual grass growth in vitro as exhibited by reduction in root growth or germination as compared to control plants.

An agar bioassay was developed Kennedy et al., 1991 (Soil Sci. Soc. Am. J. 1991 Vol.55 pp. 722-727) to screen soil isolates that selectively suppressed annual grass weeds, but did not harm other plant species. This procedure was the first step in determining those isolates that needed to be studied. To test for weed-suppressive activity, bacteria were grown in *Pseudomonas* minimal salts medium (Bolton and Elliott, 1989 *Plant and Soil*, Vol. 114, pp.269-2'78) on a gyratory shaker at 250 rpm at 22° C. (72° F.) for 32 hr. One mL of the cell culture was added to water agar plates Difco Bacto agar (Difco Laboratories, Detroit, Mich.) in a 100 by 15 mm Petri dish. Controls received 1 mL of sterile growth medium. Fifteen downy brome seeds were placed on the solid agar surface of each petri dish so that the roots would grow down through the agar. Seed collected from eastern Washington was used because this one accession of downy brome germinated within 2 days. The plates were placed in dark incubators at 15° C. (59° F.). This temperature was within the range of soil temperatures found in early spring in Washington; allowed germination and growth of the seeds; and limited microbial contaminants on the Petri dish. After 5 days, the seedlings were removed, germination recorded, and root lengths measured. Two plates were used for each isolate and the experiment was conducted three separate times. We selected the listed plant species using the Wapshere (1974) concentric spheres of related species. Wapshere's concept is a starting point for investigations of non- target plant species. Testing must be performed on all plants of economic importance in agriculture, horticulture or rangeland systems or known to be beneficial to maintenance of the ecosystem that have any reasonable likelihood of serving as hosts. This selection of additional plant species should be based upon a survey of plants closely related (same tribe or subtribe, genus or same family) to the target plant and a survey of known hosts of pathogens closely related to the microbial herbicide (Wapshere, 1974; EPA, 2011). Those strains that are inhibitory to annual grasses are then tested against desirable plants; those strains that do not negatively affect desirable plant growth in vitro are selected.

In the in vitro screening procedure, individual colonies are inoculated into a medium suitable for growing the colonies, for example, Pseudomonas minimal salts medium (PMS) described e.g., by (Bolton and Elliott, 1989, supra) and grown at a suitable temperature, e.g., about 22° C. (72° F.) until late logarithmic growth (about $10^9$ to $10^{11}$ cells $mL^{-1}$ culture medium). The cells are then treated in at least one of the following ways: (1) the culture is used directly, (2) the culture is centrifuged to obtain a substantially cell-free culture supernatant (not more than about $10^4$ cells $mL^{-1}$ of supernatant), or (3) the cell culture is centrifuged and filter sterilized to obtain a cell-free culture filtrate (no cells present). The first method quickly assays both the effect of the organism and the effect of weed-suppressive compound production by the organism on annual grass weed growth. The second method is an assay to determine the effect of weed-suppressive compound production by the organism on the growth of annual grass weed. The third method is more time consuming, but tests only the supernatant with no cells present.

Annual grass weed growth inhibition is assessed by adding to a 100 by 15 mm Petri dish a standard quantity, usually 1 mL, of the cell culture, substantially cell-free culture supernatant, or cell-free culture filtrate. A standard quantity, usually 18 mL, of 0.9% molten agar (50° C., 122° F.) is added to each Petri dish, the contents mixed, and allowed to solidify.

Generally two plates are prepared for each organism tested. Control plates are prepared by using PMS (Bolton and Elliott, 1989, supra) instead of the cell culture, substantially cell-free culture supernatant, or cell-free culture filtrate. The Petri dishes are planted with annual grass weed seeds, 15 seeds $dish^{-1}$ is convenient, and allowed to grow at a suitable temperature, e.g., 15° C. (59° F.). The plates are slanted slightly so the roots grow down and across the plate. Before root growth from the seedlings interferes with each other, about 5 days, the seedlings are pulled from the agar and root length or germination or both are recorded.

The bacteria showing significant inhibition of annual grass weed growth (length) or germination when compared to the control are then tested against desirable plant seedling growth. For the purposes disclosed herein, significant inhibition of annual grass weed in the in vitro test is typically at least about a 50% reduction in root growth (length) when compared to the control or at least a 20% reduction in germination when compared to the control.

Step. 3. Desirable Plant Bioassay

Pseudomonas fluorescens selected for their ability to inhibit growth of grass weeds using the agar bioassay disclosed in step 2 above, are then further tested using agar bioassay to determine whether or not they suppress growth of desirable plant species.

The strain selected above is assessed against desirable plants as follows: Test tubes receive a standard quantity, usually 1 mL each, of the cell culture, substantially cell-free culture supernatant, or the cell-free culture filtrate that was used in the annual grass test, and a standard quantity of 0.9% molten agar (50° C.; 122° F.), usually about 9 mL, is added to each tube, the contents mixed, and the tube slanted. Generally 10 growth tubes are prepared for each organism tested. Control tubes are prepared identically except that PMS is substituted for the cell culture, substantially cell-free culture supernatant, or the cell-free culture filtrate. When solidified, pregerminated desirable plant seeds (one per tube) are planted mid-slope on the slants and allowed to grow at a suitable temperature, e.g., 15° C. (59° F.). Before root growth reaches the bottom of the tube, approximately 3-6 days, the seedlings are pulled from the growth tubes and root length recorded. A bacterial strain is denoted as one that does not deleteriously affect desirable plant when root growth reduction of the bacterial treated desirable plant is less than 25% when compared to the control desirable plant seedlings.

Pure cultures of the bacterial strains significantly inhibiting annual grass weed growth with little or no effect on desirable plant growth are individually streaked onto a suitable medium such as King's B medium, or Nutrient Broth and selected and restreaked until the strain is pure and stable. Each individual strain is grown up and maintained so as to keep it stable such as by storing in glycerol at −10° C. (14° F.) or the cells can be freeze-dried, vacuum packed and stored at −10° C. (14° F.).

Step 4. Anti-Microbial Activity Bioassay

Antibiotics are produced by many soil microorganisms. These antibiotics are often used to impart greater competitive ability to the particular soil microbe. In our quest to find benign soil bacteria we tested the weed-suppressive bacteria for lack of antibiotic production. Our selected bacteria were screened for their ability to reduce the growth of various bacteria and fungi. The bacteria in our library of weed-suppressive bacteria do not have anti-microbial activity against our panel of microorganisms selected because they represent a wide array soil microorganisms and are found in soil. The panel consists of soil fungi (*Alternaria alternate, Chaetomium globosum, Cladosporium malorum, Cladosporium oxysporum, Fusarium avenaceum, Fusarium culmorum, Fusarium merismoides, Humicola grisea, Humicola tainanensis, Mortierella* sp., *Mucor circinelloides, Paecilomyces farinosus, Papulaspora* sp., *Penicillium* sp., *Phoma medicaginis, Phoma* sp., *Pythium* sp., *Septoria* sp., *Trichoderma* sp., *Ulocladium atrum, Ulocladium dauci, Ulocladium* sp.) and soil bacteria (*Azotobacter* spp., *Bacillus subtilis, Bradyrhizobium japonicum, Eschericia coli, Proteus vulgaris, Rhizobium leguminosarum, Staphylococcus aureus, Streptomyces* spp.).

Weed-suppressive bacteria were tested for antifungal activity by placing a 1 $cm^2$ fungal plug of the panel species in the center of 100 mm×15 mm Petri dishes of Potato Dextrose Agar and Tryptic Soy Agar. Five of the selected bacteria were inoculated with a sterile loop 2.5 cm from the fungus around the edge of the Petri dish. The plates were then incubated at 22° C. (72° F.) for 120 hr and verified every 12 hr. Zones of inhibition were measured 5 days later. The strains that inhibited proliferation of the fungus were discarded from the selected group and those that did not inhibit the fungi were selected for further study.

Selected bacteria were also tested for anti-bacterial activity using the pour plate method by adding mid-log bacterial cells of our panel of bacteria to cooled molten agar. The agar was distributed into Petri dishes and allowed to harden. The weed-suppressive bacteria were stabbed into the Petri dish agar in a grid pattern testing ten bacteria $plate^{-1}$. The plates were then incubated at 22° C. (72° F.) for 120 hr and verified every 12 hr. Zones of inhibition were measured 5 days later. If any clearing occurred, the bacteria spotted on the pour plate was not continued on in our studies. We continued to work with the bacteria that did not inhibit or change the growth of fungi and bacteria. *P.f.* ACK55, *P.f.* NKK78, and *P.f.* MAK69 did not inhibit any of these test species. (Weller, D. M., and R. J. Cook. 1983. Phytopathology, Vol. 37 pp. 463-469).

Step 5. Lack of Cell Lysis or Enzyme Assay

To study enzyme activity of bacterial strains, the strains were shaken in Nutrient Broth medium and incubated at 22° C. (72° F.) for 32 hr. Soil bacteria were assayed for cell lysis using protoplasts from lettuce and wheat roots (Rao and Prakash, 1995). Briefly, bacteria were grown in Nutrient Broth for 32 hr; shaken with protoplasts for 24 hr; and viewed under compound microscope for intact or lysed cells. Only those bacteria that resulted in intact protoplasts were continued in the program.

We surface disinfected lettuce or wheat seeds in 1:10 bleach:water, then rinsed them three times in sterile distilled water. Using aseptic technique, we placed the seeds on half-strength 'Isolation Solution' agar in Petri dishes. The seeds were incubated at 15° C. (59° F.) for 2 weeks. We removed the roots when they were 50 mm long and aseptically cut them into 2 to 3 mm sections. The root sections were added to 10 ml of sterile 'Enzyme Solution' in small sterile glass tubes and shaken on orbital shaker at 100 rpm overnight at 15° C. (59° F.). The following morning the digested material was sieved to pass a 650 µm nylon mesh using 13% sorbitol. The solution was centrifuged at 2000 rpm for 10 minutes; washed in sterile 'Isolation Solution'; and centrifuged again in 20% sucrose. The layer containing protoplasts was removed placed in a small sterile tube. 'Isolation Solution' was added to equal a 1:1 solution and mixed gently and 150 µL of protoplast solution was added to microtiter plates. Fifty µL of bacterial suspension was added to each well. The microtiter plate was shaken slowly for 24 hr at 15° C. (59° F.). We observed the protoplasts under a compound microscope for intact protoplasts indicating that the bacteria did not produce enzymes capable of lysing plant cells. Those bacteria were continued on in our selection program. If the protoplasts were lysed, then those bacteria were discarded as they produced enzymes that lyse cells. (Rao, K. S. and A. H. Prakash 1995 J. Bioscience Vol. 20 pp. 645-655).

Step 6. Protein Secretion Assay

Prokaryotic microorganisms such as *P. fluorescens* can secrete proteins to their extracellular medium or to an intracellular compartment (the periplasmic space) that lies between the inner and outer membranes. Proteins are produced for structural and mechanistic uses, while others are produced by an organism with the goal of accomplishing specific tasks. Some bacteria produce proteins that have a deleterious effect on other organisms. A bacterial protein can be toxic, causing illness or death in an organism that has been infected by the bacteria, and bacterial proteins can also bind with specific proteins of organisms to cause a variety of symptoms. There are many proteins produced by bacteria for defense and survival. Often these proteins are harmful to other soil organisms. Not all bacteria produce specific proteins in large quantities. In our investigation for a benign soil organism, we selected for bacteria that do not produce excess proteins. Our first level of selection was to find biovars of *Pseudomonas fluorescens* that were identified by phospholipid fatty acid analysis and Microbial Identification software (MIDI) as taxonomically residing in the first two biovar groups: A or B. In general, protein secretions are not produced by these biovars. In addition, we assayed the strains for their overall protein content and selected those with low protein.

The second level of selection was to test the cell-free filtrate for protein content. Any suitable method can be used (see e.g., Noble et al. (2009) Methods Enzymol. 463: 73-95). However, in an exemplary embodiment, the Bradford Assay is used. The Bradford assay, a colorimetric protein assay, is based on an absorbance shift (from 465 nm to 595 nm) of Coomassie Brilliant Blue G-250, in which under acidic conditions, the red form of the dye is converted into the blue form when bound to the protein in solution (Bradford, 1976 Anal. Biochem. 72: 248-254). Both hydrophobic and ionic interactions stabilize the anionic form of the dye, causing a visible color change. The assay is useful since the extinction coefficient of a dye-albumin complex solution is constant over a 10-fold concentration range (Zor et al., 1996 Anal. Biochem., Vol. 236 pp. 302-308).

The bacterial strains to be assayed were grown to mid-log phase (32 hr). The solution was centrifuged at 4800 g for 20 minutes to pellet the cells and supernatant was filtered through a 0.22 μm filter to remove the remaining cells. One mL of filtrate was placed in a 4 mL tube and serial dilutions of the cell-free filtrate were prepared. An aliquot of 100 μL of each of the above was added to separate test tubes. The protein standards (blank=NaCl only), 50, 100, 250, 500, 750 and 1500 μg/mL diluted with 0.15 M NaCl were prepared in 4 mL tubes using bovin serum albumin (see e.g., Zor et al., 1996, supra). Five mL of Coomassie Blue was added to each tube and mixed by vortexing for 5 seconds. After 5 minutes, the absorbance was read at 595 nm wavelength using a visible spectrophotometer. The absorbance of the standards vs. their concentration were plotted and the extinction coefficient and the concentrations of the unknown samples. The strains with absorbance less than 60 μg/g cell were carried on to the next level. *P.f.* ACK55, *P.f.* NKK78, and *P.f.* SMK69 all had protein levels less that 60 μg/g cell, illustrating a low level of protein and few deleterious secretions.

Step 7. Location of Genes Responsible for Weed-Suppression

Tn5 mutagenesis was used to determine if the genes responsible for the production of weed-suppressive compounds of *P.f.* ACK55, *P.f.* NKK78, and *P.f.* SMK69 were located on multiple locations on the chromosome. Genes that are located at multiple positions on the chromosome are less likely to be transferred to other organisms and transcribed. Previous studies had indicated that weed-suppressive compounds produced by certain strains of *Pseudomonas fluorescens* can inhibit the growth of some strains of *E. coli* (Bolton et al., 1989 Plant Soil, Vol. 114 pp. 279-287; Fredrickson and Elliott, 1985 Plant Soil, Vol. 83 pp.399-409) and wheat and downy brome (Ibekwe and Kennedy, 2009 International Journal of Environmental Technology and Management, Vol. 12 pp. 27-46).

A suicide plasmid vector pGS9 (Selvaraj and Iyer, 1983 J. Bacteriol, Vol. 156 pp. 1292-1300) was used to generate random Tn5 insertion mutants of *E. coli* donor strain (WA803) that were used to deliver the transposon. The recipients, *P.f.* ACK55, *P.f.* NKK78, and *P.f.* SMK69 were grown at 25° C. to mid-log phase in King's Medium B broth (KB; King et al., 1954 J. Lab. Clin. Med. Vol. 44 pp. 301-307). The donor, *E. coli* strain WA803, was grown at 37° C. (99° F.) to mid-log phase in Luria and Bertani (LB) broth (Maniatis et al., 1982 Molecular Cloning—A Laboratory Manual, Cold Spring Harbor Laboratory, Cold Spring Harbor, N.Y.) supplemented with kanamycin (Km) at 25 mg $L^{-1}$ to maintain Tn5. This plasmid, pGS9, is composed of a 15A replicon and the N conjugative system. Cells were centrifuged at 12,000X g for 10 min and washed twice with LB broth. Sterile saline (NaCl, 0.08%) was used for the final wash of donor cells. The donor, *E. coli* strain WA803, was chosen because of its resistance to the weed-suppressive compounds. For mating, equal volumes (0.1 mL each) of the donor and recipient cells were spotted onto nitrocellulose membranes placed on LB agar and incubated for 26 hr at 28° C. (−2.2° F.). Mutants were isolated by aseptically placing membranes into centrifuge tubes containing LB broth. After incubation, cells were washed off membranes with *Pseudomonas* Minimal Salts (PMS) broth (Bolton et al., 1989, supra), serially diluted, spread onto PMS agar plates supplemented with vitamin-free casamino acids (200 mg $L^{-1}$) and Km (100 mg L-1) and incubated at 25° C. (−39° F.) for three days for the selection of transconjugants. Transconjugants were checked for streptomycin resistance (Smr) and chloramphenicol sensitivity (Cms). In addition, Kanamycin-resistant (Kmr) transconjugants were stabbed into PMS agar containing Km (100 mg $L^{-1}$) either with or without vitamin-free Casamino Acids to screen for amino acid auxotrophs. Weed-suppressive bacteria activities were tested by growing mutants in PMS broth and performing a bioassay with downy brome seed on agar medium (Kennedy et al., 1991 Soil Science Society of American Journal, Vol. 55, pp.722-727).

Growth characteristics were determined by culturing the mutants on Sands and Rovira agar medium (Sands and Rovira, 1970 Applied Microbiology, Vol. 20, pp.513-514) and in *Pseudomonas* minimal salts broth medium (Bolton et al., 1989, supra). The mutants having colony morphology and generation times similar to that of the parental strains were maintained for additional studies. The root-suppressive activity was tested using the bioassay for downy brome-suppressive compounds (Kennedy et al., 1991, supra). Mutants were categorized by production of suppressive compounds or lack thereof and tested in DNA studies.

Chromosomal and plasmid DNA were isolated from mutants and *P.f.* ACK55, *P.f.* NKK78, and *P.f.* SMK69 by using the Qiagen DNA and plasmid preparation kits (Qiagen, USA). DNA was restricted with EcoRI at 37° C. (99° F.) for 3hr. The restricted DNA was separated through a 0.8% (w/v) agarose gel and blotted onto Hybond-N+ nylon membrane (Amersham Int., Little Chalfont, Bucks, UK). The blot was prehybridised and hybridised at 65° C. (149° F.) in 7% (w/v) Sodium Dodecyl Sulphate (SDS), 1% (w/v) Bovine Serum Albumin (BSA) and 0.5 M phosphate buffer. Blots were prehybridised for 3-5 hr before the probe was added and then hybridized for 12-18 hr. After hybridization the blot was washed in 0.1% SDS at 65° C. (149° F.).

Chromosomal DNA was isolated as described earlier from strains that were weed suppressive (WS+) and non weed suppressive (WS−). Polymerase chain reaction was done by using Ready-To-Go-Random Amplified Polymorphic DNA (Ready-To-Go-RAPD) analysis according to the manufacturer's instruction (Amersham Pharmacia Biotech, Piscataway, N.J.) with the RAPD primer 6-(5'-d[CCCGTCA-GCA]-3' SEQ ID NO:1), after testing other primers for strain differentiation. The PCR products were separated on a 2% agarose gel in a TBE buffer.

Southern blot analysis of the restriction endonuclease EcoRI digests of the different strains demonstrated unique Tn5 insertion sites in the genome of all the mutants and P.f. ACK55, P.f. NKK78, and P.f. SMK69. The bands were found in different combinations of fingerprinting patterns. Most strains shared a large portion of the band set, while a few had unique bands as indicated by the banding patterns. The WS− mutants were distributed throughout the clusters. These results showed that some Tn5 mutants are genotypically distinct from one another and that there are several genes located throughout the chromosome involved in weed-suppressive compound production based on banding pattern.

Step 8. Macrofauna, Daphnia, Lemna and Lady Bug Assay
DAPHNIA

Daphnia have a wide distribution on earth. The reproductive cycle of Daphnia is ideal for experimental assays as it is easily cultured and reaches maturity in 5 days. Daphnia are an exceptional model for studying environmental, developmental and disease processes. They occur in a highly diverse set of habitats ranging from freshwater lakes to saline ponds. We tested eight dilutions of mid-log cultures of P.f. ACK55, P.f. NKK78 and P.f. SMK69 and controls to determine if the bacteria affected Daphnia. Daphnia magna (Carolina Biological Supply, Burlington, N.C.) stock females bearing embryos were grown at 20° C. (68° F.) in 400-mL beakers containing 300 mL of sterile aerated spring water at pH 7.3 and powdered Spirulina as a food source. Ten young Daphnia were chosen from these cultures and placed in each treatment beaker using a plastic, disposable pipette with a 5-mm diameter. Bacteria were grown in Tryptic Soy Broth to mid-log phase (32 hr) at 20° C. (68° F.). Bacteria were serially diluted into eight tubes (Log 1 through 8) and 1.0 mL of each dilution was added to the beakers every day for 4 days. Controls consisted of the medium alone. Five replications were used throughout. Beakers were incubated at 20° C. (68° F.). Mortality was monitored hourly for 8 hr and then again at 24 hr. There were no differences among the various strains and treatments. The mortality of Daphnia magna was not affected by P.f. ACK55, P.f. NKK78 or P.f. SMK69 at any dilution.
LEMNA We tested eight dilutions of mid-log cultures of P.f. ACK55, P.f. NKK78 and P.f. SMK69 and controls to determine if the bacteria affected Lemna growth. Lemna (Lemna minor) were harvested from local roadside ditches near Pullman, Wash. and placed in an aerated tank. Fifty Lemna plants of similar size were placed in Petri dishes containing 12 mL spring water and a small aeration needle. Bacteria were grown in Tryptic Soy Broth at 20° C. (68° F.) to mid-log phase (32 hr; 1 x $10^8$ cells $mL^{-1}$). Bacteria were serially diluted into eight tubes (Log 1 through 8) and 0.5 mL of each dilution was added to a 100×15 mm Petri dish every day for 4 days. Controls consisted of the medium alone. Five replications were used throughout. Petri dishes were incubated at 20° C. (68° F.). After fourteen days the water was decanted and the Lemna plants were dried at 60° C. (120° F.) and then weighed. There were no differences among the various strains and treatments. The growth of Lemna minor was not affected by P.f. ACK55, P.f. NKK78 or P.f. SMK69 at any dilution.
LADY BUGS We tested eight dilutions of mid-log cultures of P.f. ACK55, P.f. NKK78 and P.f. SMK69 and controls to determine if the bacteria affected lady bug mortality. Six cups of lady bugs (Hippodamia spp.) were captured from local swarms at Pullman, Wash. in the spring of the year. Approximately 100 lady bugs were placed in each quart canning jars with a cloth covering the opening and secured by a jar ring. The lady bugs were fed fresh macerated grapes daily and kept moist with a sterile water spritz twice daily. Bacteria were grown in Tryptic Soy Broth at 20° C. (68° F.) to mid-log phase (32 hr; 1×$10^8$ cells $mL^{-1}$). Bacteria were serially diluted into eight tubes (Log 1 through 8) and 1 mL of each dilution was added to the macerated grapes every day for 4 days. Controls consisted of the medium alone. Five replications were used throughout. The canning jars were incubated at 20° C. (68° F.). After seven and fourteen days the live and dead lady bugs were counted. There were no differences among the various strains and treatments. The growth of the lady bugs was not affected by P.f. ACK55, P.f. NKK78 or P.f. SMK69 at any dilution.

Step 9. Survival with Freeze Drying Assay

Bacteria were screened for their ability to withstand freeze drying. Bacteria were grown in Tryptic Soy Broth to mid-log phase (32 hr) at 20° C. (68° F.) and centrifuged at 3500 g for 20 minutes. Cells were placed in a plastic bag and frozen for 48 hr. The cells were freeze dried and bacterial counts were taken before and after freeze drying to determine those bacteria that survive the freeze drying and have adequate viable populations. P.f. ACK55, P.f. NKK78 and P.f. SMK69 population numbers after free drying were only 0.5 to 1 log lower than that before freeze drying.

Step 10. Weed Suppression in the Growth Chamber Screening

Bacteria that have fulfilled the requirements of those characteristics previously tested are then subjected to a screening in soil by separately growing annual grass weed plants and desirable plants in pots in a growth chamber or greenhouse in the presence of the selected bacteria. In this step, those strains are selected which, at a particular concentration, inhibit annual grass weed without deleteriously affecting desirable plant.

In this test, pots are filled with soil and seeded with annual grass weed or with desirable plant seeds. We have found that 6.4 cm diameter by 7.6 cm deep plastic pots seeded with 6-10 dehusked annual grass weed seeds and 7.6 cm diameter by 15.2 cm deep plastic pots seeded with 4 seeds of the desirable plants for initial testing are convenient sizes for growth chamber or greenhouse studies. Any soil suitable for growth chamber studies can be used. One exemplary soil is Ritzville silt loam amended with 20% sand by weight. It is not necessary to surface-sterilize the seeds prior to planting.

The amount of bacteria per annual grass weed seed in the test pots is selected so as to optimize the selection of field-effective strains and minimize the selection of field-ineffective strains. We have found that a range of $10^8$ to $10^{10}$ colony forming units (CFU) of the test strain per annual grass weed test pot is applied to the soil surface. One convenient method is putting the test strain in a liquid such as distilled water or PMS and dripping the liquid on to the soil surface. Desirable plant seeds are grown in the presence of $10^8$ to $10^{10}$ CFU of the test strain $pot^{-1}$ with 4 seeds to assess the effect of the bacteria on desirable plant. Separate annual grass weed and desirable plant controls are prepared identical to the test samples except without bacterial treatment.

The soil is wetted to provide good plant growth, and the pots incubated in the growth chamber. We have found that a 14-hr day at 18° C. (64.4° F.) and a 10-hr night at 13° C. (55.4° F.) is suitable. After about 3 to 4 weeks, the annual grass weed and desirable plant seedlings are pulled up and the roots washed with water until free of soil. The roots and shoots of the annual grass weed and desirable plant seedlings are excised and roots or shoots or both dried to remove water so that a comparison to control plants can be made. Drying at 60° C. (140° F.) for 48 hr is suitable.

Evaluation of Seedlings in the Growth Chamber Test

To evaluate the bacterial treatment, root or shoot dry weight of the annual grass weed plants is compared with the root or shoot dry weight of the control annual grass weed plants. Bacterial strains that cause the treated annual grass weed seedlings to have reduced root growth (reduced root dry weight when compared to the control) of at least 30% or that cause the treated annual grass weed seedlings to have reduced shoot growth (reduced shoot dry weight when compared to the control) of at least 30% are considered inhibitory to annual grass weed in this test.

To evaluate the bacterial treatment on desirable plant, root dry weight or shoot dry weight of the desirable plant plants are compared with the control desirable plant plants. For the purposes of this invention, a bacterial strain is denoted as one that does not deleteriously affect the desirable plant by reduction in root growth (root dry weight) or shoot growth (shoot dry weight) of the bacterial treated desirable plant is less than 10% when compared to the control desirable plant seedlings.

Step 11. Does Not Injure Desirable Plant Species Such As Crops of Economic Importance and Native or Near-Native Plant Species Bacteria that have fulfilled the requirements of those characteristics previously tested are then subjected to a screening in soil by separately growing annual grass weed plants and desirable plants in pots in a growth chamber or greenhouse in the presence of the bacteria. In this step, those strains are selected that, at a particular concentration, inhibit annual grass weed without deleteriously affecting desirable plant.

In this test, pots are filled with soil and seeded with annual grass weed or with desirable plant seeds. We have found that 6.4 cm diameter by 7.6 cm deep plastic pots seeded with 6-10 dehusked annual grass weed seeds and 7.6 cm diameter by 15.2 cm deep plastic pots seeded with 4 seeds of the desirable plants for initial testing are convenient sizes for growth chamber or greenhouse studies. Any soil suitable for growth chamber studies can be used. One exemplary soil is Ritzville silt loam amended with 20% sand by weight. It is not necessary to surface-sterilize the seeds prior to planting.

The amount of bacteria per annual grass weed seed in the test pots is selected so as to optimize the selection of field-effective strains and minimize the selection of field-ineffective strains. We have found that a range of $10^8$ to $10^{10}$ CFU of the test strain per annual grass weed test pot is applied to the soil surface. One convenient method is putting the test strain in a liquid such as distilled water or PMS and dripping the liquid on to the soil surface. Desirable plant seeds are grown in the presence of $10^8$ to $10^{10}$ CFU of the test strain $pot^{-1}$ with 4 seeds to assess the effect of the bacteria on desirable plant. Separate annual grass weed and desirable plant controls are prepared identical to the test samples except without bacterial treatment.

The soil is wetted to provide good plant growth, and the pots incubated in the growth chamber. We have found that a 14-hr day at 18° C. (−7.8° F.) and a 10-hr night at 13° C. (55.4° F.) is suitable. After about 3 to 4 weeks, the annual grass weed and desirable plant seedlings are pulled up and the roots washed with water until free of soil. The roots and shoots of the annual grass weed and desirable plant seedlings are excised and roots or shoots or both dried to remove water so that a comparison to control plants can be made. Drying at 60° C. (140° F.) for 48 hr is suitable.

Evaluation of Seedlings in the Growth Chamber Test:

To evaluate the bacterial treatment, root or shoot dry weight of the annual grass weed plants is compared with the root or shoot dry weight of the control annual grass weed plants. Bacterial strains that cause the treated annual grass weed seedlings to have reduced root growth (reduced root dry weight when compared to the control) of at least 30% or that cause the treated annual grass weed seedlings to have reduced shoot growth (reduced shoot dry weight when compared to the control) of at least 30% are considered inhibitory to annual grass weed in this test.

To evaluate the bacterial treatment on desirable plant, root dry weight or shoot dry weight of the desirable plant plants are compared with the control desirable plant plants. For the purposes of this invention, a bacterial strain is denoted as one that does not deleteriously affect desirable plants when reduction in root growth (root dry weight) or shoot growth (shoot dry weight) of the bacterial treated desirable plant is less than 10% when compared to the control desirable plant seedlings.

Step 12. Screening of Weed Suppression by the Bacterial Strains in the Field

Bacterial strains selected in the previous step are next tested in the field. We have found that treatment plots consisting of 3×3 meters with 5 replications are suitable. The control (non-treatment) should be adjacent to the treatment plot so that treatment and non-treatment plots have similar soil conditions. For the field test, it is preferred that annual grass weed plants be grown in plots that are substantially free of other weeds so that variability due to the presence of other weeds is reduced. If no grass weeds are present in the plot area, the plots can be seeded to the specific annual grass weed with 50 to 75 seeds $m^{-2}$. Individual bacterial strains to be tested are applied to the soil as a spray treatment. The treatment is applied in the fall with moisture imminent. The bacteria must be applied to moist soil to insure survival of the organisms. For the spray treatment, the test strain in a liquid such as distilled water or PMS is sprayed on to the soil to provide a concentration of about $10^8$ to $10^{12}$ CFU of the test strain $m^{-2}$. Control plots are treated identical to the test plot except that no bacteria are applied. To ensure statistical significance, each treatment is replicated a minimum of five times.

Individual strains of bacteria that inhibited annual grass weed in the growth chamber and field tests without deleteriously affecting desirable plant are cultured by standard methods for a time to grow sufficient bacteria to treat the field area, generally about 24-48 hr. Plots seeded to the desirable plant (about 100 to 150 seeds $m^{-2}$) are seeded beside or with the annual grass weed plots and the test organisms are sprayed on the plots to provide a concentration of about $10^8$ to $10^{12}$ CFU of the test strain $m^{-2}$. The control plants receive identical treatment except that no bacteria are applied. To ensure statistical significance, each treatment is replicated a minimum of five times.

Evaluation of Seedlings in the Field Test:

To assess the effect of the bacterial treatment in the inhibition of annual grass weed in the field, after adequate growth has occurred, e.g., about the 3-to 5-leaf stage, and at least one of the following is obtained: root dry weight, shoot dry weight, or stand (numbers of plant $m^{-2}$). Bacterial strains that cause the treated annual grass weed plants to average a reduction in root growth (root dry weight), reduction in shoot growth (shoot dry weight), or reduction in stand of at least 20% when compared to control annual grass weed plants are considered inhibitory to annual grass weed in the field test. To assess the effect of the bacterial treatment on desirable plant, at least one of the following is obtained: root dry weight, shoot dry weight, or stand. Those bacterial strains that cause desirable plants to average less than 10% reduction in root growth (root dry weight), shoot growth (shoot dry weight) or stand compared to control desirable plant are defined as not deleteriously affecting the crop.

Step 13. Screening of an Adverse Effect by the Bacterial Strains to Desirable Plants in the Field Bacterial strains selected in the previous step are next tested in the field. We have found that treatment plots consisting of 3×3 meters with 5 replications are suitable. The control (non-treatment) should be adjacent to the treatment plot so that treatment and non-treatment plots have similar soil conditions. For the field test, it is preferred that annual grass weed plants be grown in plots that are substantially free of other weeds so that variability due to the presence of other weeds is reduced. If no grass weeds are present in the plot area, the plots can be seeded to the specific annual grass weed with 50 to 75 seeds m$^{-2}$. Individual bacterial strains to be tested are applied to the soil as a spray treatment. The treatment is applied in the fall with moisture imminent. The bacteria must be applied to moist soil to insure survival of the organisms. For the spray treatment, the test strain in a liquid such as distilled water or PMS is sprayed on to the soil to provide a concentration of about $10^8$ to $10^{12}$ CFU of the test strain m$^{-2}$. Control plots are treated identical to the test plot except that no bacteria are applied. To ensure statistical significance, each treatment is replicated a minimum of five times.

Individual strains of bacteria that inhibited annual grass weed in the growth chamber and field tests without deleteriously affecting desirable plant are cultured by standard methods for a time to grow sufficient bacteria to treat the field area, generally about 24-48 hr. Plots seeded to the desirable plant (about 100 to 150 seeds m$^{-2}$) are seeded beside or with the annual grass weed plots and the test organisms are sprayed on the plots to provide a concentration of about $10^8$ to $10^{12}$ CFU of the test strain m$^{-2}$. The control plants receive identical treatment except that no bacteria are applied. To ensure statistical significance, each treatment is replicated a minimum of five times.

Evaluation of Seedlings in the Field Test:

To assess the effect of the bacterial treatment in the inhibition of annual grass weed in the field, after adequate growth has occurred, e.g., about the 3-to 5-leaf stage, and at least one of the following is obtained: root dry weight, shoot dry weight, or stand (numbers of plant m$^{-2}$). Bacterial strains that cause the treated annual grass weed plants to average a reduction in root growth (root dry weight), reduction in shoot growth (shoot dry weight), or reduction in stand of at least 20% when compared to control annual grass weed plants are considered inhibitory to annual grass weed in the field test. To assess the effect of the bacterial treatment on desirable plants, at least one of the following is obtained: root dry weight, shoot dry weight, or plant stand count. Those bacterial strains that cause desirable plants to average less than 10% reduction in root growth (root dry weight), shoot growth (shoot dry weight) or plant stand count compared to control desirable plant are defined as not deleteriously affecting the crop.

Step 14. Do Not Survive in Field Soil for More than 3 Years

Survival of the bacterium is necessary for biocontrol efficacy, but we do not want the bacteria to persistent longer than 3 yr in the soil. The bacterium needs to survive to inhibit the downy brome, and survival in the first weeks after application to soil is imperative. The naturally occurring P.f. ACK55 cannot be distinguished from other Pseudomonas spp. and the multi-loci genes responsible for suppression preclude use of molecular markers (Ibekwe et al., 2009, supra). Pseudomonas fluorescens strain ACK55rif (P.f. ACK55 resistant to 100 mg L$^{-1}$ rifampicin) can be applied to the soil to selectively isolate P.f. ACK55rif from that soil and distinguish it from other soil organisms. Rifampicin resistant bacteria are not present in the soils at most field locations. We will apply P.f. ACK55rif, in the same manner as P.f. ACK55 with the same treatments, to subplots to determine the survival and population numbers of P.f. ACK55. Roots and soil will be sampled in spring and fall to determine soil and root colonization by P.f. ACK55rif. Enumeration of P.f. ACK55rif will be determined on Pseudomonas minimal salts agar (Bolton and Elliott, 1989 Plant and Soil, Vol. 114, pp.269-2'78) amended with rifampicin using automated dilution and plating (Microbiology International, Frederick, Md.). P.f. ACK55rif populations will be followed over time and ANOVA will be used to determine treatment differences.

III. Using Weed-Suppressive Bacteria

A. General

As discussed above, weed-suppressive bacteria applied to seed and/or soil in an inhibitory amount, control invasive grass weeds by inter alia inhibiting radicle formation, root growth and tiller initiation of the target grass weeds, while not hurting native plants or crops. Thus, the use of weed-suppressive bacteria provides means for reducing invasive weeds in e.g., rangeland, cropland, pasture, turf, sod production, golf courses, road sides and road cuts, construction sites, and right-of-ways (road, rail, pipeline, electrical), etc, while limiting tillage and chemical use.

In exemplary embodiments, weed-suppressive bacteria such as e.g., P.f. ACK55 are delivered as a coating on the seeds of desirable plants (e.g., wheat, perennial bunchgrass, sagebrush). In another exemplary embodiment, weed-suppressive bacteria are pelleted or encapsulated prior to delivery. In some exemplary embodiments, pelleting and/or encapsulation increase bacterial survival rates.

The active populations of weed-suppressive bacteria are reduced in hot, dry summers and they enter a dormancy phase. Accordingly, application in late spring or summer will not allow the bacterium to establish in the soil and will result in low weed suppression. Thus, typically, weed-suppressive bacteria are applied in the fall so that they establish in the soil microbial community as weather cools and rainfall begins. Indeed, weed-suppressive bacteria that move with water to below the soil surface have increased chance of survival and establishment.

The numbers of weed-suppressive bacteria increase during cold temperatures, unlike most soil bacteria. Thus, typically, weed-suppressive bacteria compete less well with other soil bacteria when temperatures are above 4.4° C. (40° F.). However, effective establishment is still achieved at temperatures up to about 15.6° C. (60° F.) especially if water is present. Accordingly, weed-suppressive bacteria are typically applied to soil when temperatures are in a range that is between about 1.7° C. (35° F.) to about 15.6° C. (60° F.). Therefore, in one exemplary embodiment, weed-suppressive bacteria are applied to soil when daytime temperatures are below 10° C. (50° F.).

Because the presence of water facilitates the survival and establishment of weed-suppressive bacteria, lack of rainfall within two weeks of application may reduce weed suppression. Therefore, in one exemplary embodiment, an initial application of weed-suppressive bacteria is made in the late fall when daily high temperatures are less than about 12.8° C. (55° F.) and more than 0.2 inches of rain is imminent or expected within the next 2 weeks.

Weed-suppressive bacteria do not follow the normal herbicide paradigm. Indeed, in the first few years after field application, the bacteria inhibit plant growth and numbers by 20 to 50% and this inhibition increases with time. In one exemplary embodiment, a single application of weed-suppressive bacteria results in almost complete suppression of downy brome within five to seven years.

B. Dosage

The dosage rate of weed-suppressive bacteria is any amount that that is effective for controlling invasive grass weeds (i.e. an inhibitory amount). In one exemplary embodiment, a pint of the actively growing weed-suppressive bacteria e.g., *P.f.* ACK55 is applied acre$^{-1}$ of soil/land to be treated is an effective dosage for control of invasive grass weeds. In another exemplary embodiment, 2 g of freeze-dried weed-suppressive bacteria acre$^{-1}$ is an effective dosage for almost complete suppression of downy brome over several years. In still another exemplary embodiment, 40 g of freeze-dried material dissolved in 400-100 gallons of water is effective for controlling invasive grass weeds when the resulting solution is applied to 20 acres as a concentrated spray.

In still another exemplary embodiment, freeze-dried weed-suppressive bacteria are applied to seeds of desired crops at a concentration of $10^8$ bacteria seed$^{-1}$.

Typically, weed-suppressive bacteria are applied to the soil at rates higher than is needed for weed inhibition, because as with any introduced organism there is a decline after application. Thus, the exemplary doses provided above provide inhibitory amounts of weed-suppressive bacteria, lower doses or higher doses may be used at the discretion of the land manager or other person having ordinary skill in the art and access to this disclosure.

IV. Kits

In an exemplary embodiment, kits comprising weed-suppressive *Pseudomonas fluorescens* strains are provided for controlling invasive grass weeds. The kits typically include, inter alia, a weed-suppressive *Pseudomonas fluorescens* bacterial strain and written instructions for using the kit to control invasive grass weeds.

IV. Deposit Information

A Budapest Treaty deposit of *Pseudomonas fluorescens* strain ACK55, disclosed herein and recited in the appended claims has been made with the Agricultural Research Service Culture Collection (NRRL), National Center for Agricultural Utilization Research, Agricultural Research service, U.S. Department of Agriculture, 1815 North University Street, Peoria Ill. 61604, U.S.A. The date of deposit was Aug. 15, 2013. All restrictions upon the deposit have been irrevocably removed, and the deposit is intended to meet all of the requirements of 37 C.F.R. 1.801-1.809. The NRRL accession number is NRRL B-50848. The material description is: *Pseudomonas fluorescens* biovar B strain ACK55. The deposit will be maintained in the depository for a period of 30 years, or 5 years after the last request, or for the effective life of the patent, whichever is longer, and will be replaced as necessary during that period.

A Budapest Treaty deposit of *Pseudomonas fluorescens* NKK78, disclosed herein and recited in the appended claims has been made with the Agricultural Research Service Culture Collection (NRRL), National Center for Agricultural Utilization Research, Agricultural Research service, U.S. Department of Agriculture, 1815 North University Street, Peoria Ill. 61604, U.S.A. The date of deposit was Aug. 15, 2013. All restrictions upon the deposit have been irrevocably removed, and the deposit is intended to meet all of the requirements of 37 C.F.R. 1.801-1.809. The NRRL accession number is NRRL B-50849. The material description is: *Pseudomonas fluorescens* biovar A strain NKK78. The deposit will be maintained in the depository for a period of 30 years, or 5 years after the last request, or for the effective life of the patent, whichever is longer, and will be replaced as necessary during that period.

A Budapest Treaty deposit of *Pseudomonas fluorescens* strain SMK69, disclosed herein and recited in the appended claims has been made with the Agricultural Research Service Culture Collection (NRRL), National Center for Agricultural Utilization Research, Agricultural Research service, U.S. Department of Agriculture, 1815 North University Street, Peoria Ill. 61604, U.S.A. The date of deposit was Aug. 15, 2013. All restrictions upon the deposit have been irrevocably removed, and the deposit is intended to meet all of the requirements of 37 C.F.R. 1.801-1.809. The NRRL accession number is NRRL B-50850. The material description is: *Pseudomonas fluorescens* biovar A/B strain SMK69. The deposit will be maintained in the depository for a period of 30 years, or 5 years after the last request, or for the effective life of the patent, whichever is longer, and will be replaced as necessary during that period.

The following examples are offered to illustrate, but not to limit the invention.

EXAMPLES

Example 1

The following example illustrates several methods for the application of inhibitory amounts of weed-suppressive bacteria to soil.

Method 1:

A freeze-dried powder was dissolved in water and sprayed on the soils surface in an amount effective for suppressing growth of downy brome/cheatgrass. This concentration was not likely to harm other plant species.

Forty grams of *P.f.* ACK55 were dissolved in water for each 20 acres. The composition was mixed to form a solution and the resulting solution was sprayed over the entire soil surface. Coverage characteristics of the spray equipment are used to determine the volume of water needed. Use 10 to 30 gallons of solution acre$^{-1}$ for conventional tillage or direct seed application. For other applications, use 15 to 50 gallons acre$^{-1}$ of spray solution. If there is dense vegetation or residue then use 20 to 50 gallons acre$^{-1}$ of spray solution. For a dilute spray use 50 to 200 gallons of spray solution acre$^{-1}$. For aerial application use 5 to 20 gallons of spray solution acre$^{-1}$. Once mixed with water use within 24 hr.

Optimum conditions for application are cool air temperatures and wet conditions. Hot and dry conditions and dry soil surface at application limit the effectiveness of the application of this bacterium. Thus, for best results, the weed-suppressive *P.f.* ACK55 is applied in the fall or very early spring before germination and when day-time temperatures are below 10° C. (50° F.).

Method 2: Seed

Use 40 grams of freeze-dried material for each 20 acres. Apply bacteria to seed at $10^8$ cells per seed using a seed coater. Apply the material as a slurry in 10 oz. water per 60 lb. seed to seed rotating in a drum. Direct drill or broadcast seed at recommended seeding rates, which could be 60 lb. acre$^{-1}$ wheat seed or 30 lb. acre$^{-1}$ nativeseed. Species of seed can be crop or native plant or other species. Treated seed must not be used for or mixed with food or animal feed.

Method 3: Liquid

For downy brome suppression, apply 40 grams in 400-1000 gallons 20 acres$^{-1}$ as a concentrated spray. Final minimum concentration $10^8$ cells m$^{-2}$ soil surface.

Example 2

The following Example illustrates control of downy brome in field studies.

Field tests were conducted to determine the effect of *P.f.* ACK55 on the reduction of downy brome in the field. This bacterium does not follow the normal herbicide paradigm. In the first few years after field application, the bacteria inhibit weed growth and numbers by 20 to 50% and this inhibition increased with time. In cropland studies, the bacteria suppressed the weed and allowed the wheat be more competitive that then in turn reduced the downy brome further. In long-term rangeland field trials in the Pacific Northwest, application of the bacteria resulted almost complete suppression of downy brome five to seven years after a single application. With the reduction of downy brome, other plant species like Sandberg bluegrass, Indian rice grass, squirrel tail, or other bunch grasses increased and plant biodiversity changed. In these studies, there was little suppression of downy brome in the first year after fall application. For each of these 6 sites we see a gradual decline in the populations of downy brome until after 5 years when the bacterium has almost eliminated the downy brome. The bacterium reduces the seed bank. In addition, at each site the populations of more desirable plant species increase as the downy brome becomes less competitive. The bacteria plus the native plant, turf or wheat interact to reduce the downy brome.

Standard Operating Procedures- Field Studies

A. Growth medium

The bacterium is grown in Tryptic Soy Broth or Tryptic Soy Agar for 32 hr and harvested by centrifugation (5,000g for 10 min.) and freeze dried (10 hr).The freeze dried material was vacuum packed and stored at 0 to -80° C. (32 to -112° F.).

B. USDA-ARS Kennedy Protocol for Field Trial Spray Application

We evaluated the effect of USDA-ARS *P.f.* ACK55 on downy brome, medusahead, or jointed goatgrass growth across five years. Field experiment compare *P.f.* ACK55 sprayed on the surface of soil and residue with the non-treated control. The bacterium is sprayed in the fall of the year. *P.f.* ACK55 was stored in the original container at temperatures less than 4.4° C. (40° F.). The product is vacuum-packed, frozen and stored at less than 0° C. (32° F.). We store the container unopened or vacuum-packed in the freezer at −80° C. (−112° F.) until ready to apply. We carried the material to the field on ice or in portable refrigerator.

The application was in the late fall when daily high temperatures were less than 12.8° C. (55° F.) and more than 0.2 in of rain was imminent or rain was expected to fall within the next 2 weeks. For medusahead suppression, we applied 2 g of freeze-dried bacteria. The plot area is fenced to exclude cattle grazing for 360 days.

We followed these guidelines:

We used appropriate PPE equipment (eye protection, long sleeve shirt, gloves, long pants, boots with socks; respirator only if working with dry powder).

Before opening the package, we kneaded the packet to break up any lumps and pulled the product away from the sides of the package. We completely empty the packet into application equipment by shaking and tapping sides and bottom to loosen clinging particles. If water-dissolvable packets are use, open packet and place capsule in spray tank (no respirator needed).

USDA-ARS *P.f.* ACK55 was diluted in 20-50 gallon acre$^{-1}$ as a concentrated spray. The final minimum concentration will be $10^8$ cells m$^{-2}$ soil surface. We dilute with non-chlorinated water, such as well water. We used a spray vehicle at 4 mph with wide nozzles or back pack sprayer also with wide nozzles. In high brush, a back pack sprayer is needed to make sure the spray reaches underneath the brush canopy.

Field data were collected in the spring of each year in 10 random 0.5 m$^2$ square subplots of every treatment. We sampled annual weed percent cover, number of annual weed reproductive tillers, and aboveground biomass. The sampled subplots were marked with a subsurface tracking device and GIS coordinates recorded. Each plot and subplot was digitally photographed from several vantage points for additional data collection back in the laboratory. Survival of the bacteria is assessed throughout the season as described above. Material can be sanitized with a 1:10 solution of bleach to water or steamed or autoclaved to kill any remaining active bacterial cells.

C. USDA-ARS Kennedy Protocol for Field Trial Seed Application

We evaluated the effect of USDA-ARS *P.f.* ACK55 on downy brome, medusahead, or jointed goatgrass growth across five years. *P.f.* ACK55 is stored in the original container at temperatures less than 4.4° C. (40° F.). The product was vacuum-packed, frozen and stored at less than 0° C. (32° F.). We stored the container unopened or vacuum-packed in the freezer at −80° C. (−112° F.) until ready to apply. We carry the material to the field on ice or in portable refrigerator. Field experiments compare *P.f.* ACK55 coated on seed of desirable plants. Control plots are seeded with non-treated control seed. The seed coated with bacteria or the untreated control seed were drill seeded or broadcast in the fall of the year. The application timing is less critical than spray application, but is in the late fall when daily high temperatures are less than 12.8° C. (55° F.) and more than 0.2 in of rain was imminent or rain was expected to fall within the next 2 weeks. For annual weed suppression, we applied 2 g of freeze-dried bacteria to 500 L of water with mixing for each acre of seed. The slurry is applied to the seed as a mist and the seed mixed in a small concrete mixer. Optimum seeding rate is 60 lbs winter wheat seed for 1 acre or 30 lbs native seed acre$^{-1}$.

We followed these guidelines:

We use appropriate PPE equipment (eye protection, long sleeve shirt, gloves, long pants, boots with socks; respirator only if working with dry powder).

Before opening the package, we knead the packet to break up any lumps and pull the product away from the sides of the package. We completely empty the packet into application equipment by shaking and tapping sides and bottom to loosen clinging particles. If water-dissolvable packets are use, open packet and place capsule in container of water (no respirator needed).

The final minimum concentration was $10^8$ cells m$^{-2}$ seed. We diluted with non-chlorinated water such as well water.

Field data were collected in the spring of each year in 10 random 0.5 m$^2$ square subplots of every treatment. We sample annual weed percent cover, number of annual weed reproductive tillers, and aboveground biomass. The sampled subplots are marked with a subsurface tracking device and GIS coordinates recorded. Each plot and subplot is digitally photographed from several vantage points for additional data collection back in the laboratory. Survival of the bacteria is assessed throughout the season as described above.

We do not reuse or refill the container. We spray with bleach before disposing of empty container in a landfill. Material can be sanitized with a 1:10 solution of bleach to water or steamed or autoclaved to kill any remaining active bacterial cells.

Data are shown in FIG. 1.

What is claimed is:

1. A method for reducing the growth of downy brome (cheatgrass, *Bromus tectorum* L.), medusahead (*Taeniatherum caput medusae* (L.) Nevski), andor jointed goatgrass (*Aegilops cylindrica* L.), in an area of land, the method comprising applying approximately $10^8$ CFU/m$^2$ to approximately $10^9$ CFU/m$^2$ of one or more weed-suppressive *Pseudomonas fluorescens* strains to the area of land to reduce the growth of said downy brome, medusahead, andor jointed goatgrass; wherein said weed-suppresive *P. fluorescens* strain is selected from the group consisting of *P. fluorescens* strain ACK55 (NRRL accession number NRRL B-50848), *P. fluorescens* strain NKK78 (NRRL accession number NRRL B-50849), *P. fluorescens* strain SMK69 (NRRL accession number NRRL B-50850) and combination thereof.

2. The method of claim 1, wherein said applying is accomplished by mixing said one or more weed-suppressive *P. fluorescens* strains into soil of the land.

3. The method of claim 1, wherein said applying is accomplished by spraying said one or more weed-suppressive *P. fluorescens* strains onto the soil of the land.

\* \* \* \* \*

SEQUENCE LISTING

```
<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: Primer

<400> SEQUENCE: 1
cccgtcagca                                                              10
```